(12) United States Patent
Voisard et al.

(10) Patent No.: US 8,932,357 B2
(45) Date of Patent: Jan. 13, 2015

(54) INTERVERTEBRAL IMPLANT

(75) Inventors: Cyril Voisard, Langendorf (CH);
Markus Kraft, Oberdorf (CH); Beat Lechmann, Bettlach (CH)

(73) Assignee: DePuy Synthes Products, LLC, Raynham, MA (US)

( * ) Notice: Subject to any disclaimer, the term of this patent is extended or adjusted under 35 U.S.C. 154(b) by 81 days.

(21) Appl. No.: 13/270,371

(22) Filed: Oct. 11, 2011

(65) Prior Publication Data

US 2012/0095561 A1    Apr. 19, 2012

Related U.S. Application Data

(60) Provisional application No. 61/392,638, filed on Oct. 13, 2010.

(51) Int. Cl.
*A61F 2/44*       (2006.01)
*A61B 17/06*      (2006.01)
A61B 17/064      (2006.01)
*A61B 17/86*      (2006.01)
*A61F 2/30*       (2006.01)

(52) U.S. Cl.
CPC .......... *A61F 2/442* (2013.01); *A61B 17/06166* (2013.01); *A61B 17/0642* (2013.01); *A61B 17/8605* (2013.01); *A61F 2002/30062* (2013.01); *A61F 2002/3038* (2013.01); *A61F 2002/30433* (2013.01); *A61F 2002/30448* (2013.01); *A61F 2002/30449* (2013.01); *A61F 2002/30461* (2013.01); *A61F 2002/30492* (2013.01); *A61F 2002/30565* (2013.01);
(Continued)

(58) Field of Classification Search
CPC .......... A61F 2/442; A61F 2310/00155; A61F 2002/30062; A61F 2002/3038; A61F 2002/30433; A61F 2002/30448; A61F 2002/30449; A61F 2002/30461; A61F 2002/30492; A61F 2002/30565; A61F 2002/30604; A61F 2002/308; A61F 2002/30805; A61F 2002/30808; A61F 2002/30812; A61F 2002/30828; A61F 2002/30831; A61F 2002/30835; A61F 2210/0014; A61F 2310/00017; A61F 2310/00023; A61F 2310/00029; A61F 2310/00041; A61F 2310/00047; A61F 2310/00065; A61F 2310/00071; A61F 2310/00077; A61F 2310/00083; A61F 2310/00107; A61B 17/06166; A61B 17/8605
USPC ........................................... 623/17.11–17.16
See application file for complete search history.

(56) References Cited

U.S. PATENT DOCUMENTS 4,874,389 A * 10/1989 Downey ............... 623/17.16
5,011,497 A *  4/1991 Persson et al. ......... 623/23.41
(Continued)

FOREIGN PATENT DOCUMENTS

EP        0697200     2/1996
WO     WO 98/56317  12/1998
(Continued)

OTHER PUBLICATIONS

International Patent Application No. PCT/US2011/055670: International Search Report dated Feb. 7, 2012, 2 pages.

*Primary Examiner* — Pedro Philogene
(74) *Attorney, Agent, or Firm* — Baker & Hostetler LLP

(57) ABSTRACT

A method for fixation of an intervertebral implant includes the steps of: a) applying a spreading force to a first and second adjacent vertebral bodies; b) removing the intervertebral disc between the adjacent first and second vertebral bodies; c) inserting a shaft of the bone anchors into the vertebral bodies, and fixing a head of the bone anchors to an intervertebral implant.

33 Claims, 9 Drawing Sheets

(52) U.S. Cl.
CPC .... *A61F 2002/30604* (2013.01); *A61F 2002/308* (2013.01); *A61F 2002/30805* (2013.01); *A61F 2002/30808* (2013.01); *A61F 2002/30812* (2013.01); *A61F 2002/30828* (2013.01); *A61F 2002/30831* (2013.01); *A61F 2002/30835* (2013.01); *A61F 2210/0014* (2013.01); *A61F 2310/00017* (2013.01); *A61F 2310/00023* (2013.01); *A61F 2310/00029* (2013.01); *A61F 2310/00041* (2013.01); *A61F 2310/00047* (2013.01); *A61F 2310/00065* (2013.01); *A61F 2310/00071* (2013.01); *A61F 2310/00077* (2013.01); *A61F 2310/00083* (2013.01); *A61F 2310/00107* (2013.01); *A61F 2310/00113* (2013.01); *A61F 2310/00119* (2013.01); *A61F 2310/00149* (2013.01); *A61F 2310/00155* (2013.01)
USPC ........................................................ 623/17.16

(56) References Cited

U.S. PATENT DOCUMENTS

| | | | | |
|---|---|---|---|---|
| 7,008,452 | B2 * | 3/2006 | Hawkins | 623/17.11 |
| 8,328,847 | B2 * | 12/2012 | Ainsworth et al. | 606/246 |
| 8,357,201 | B2 * | 1/2013 | Mayer et al. | 623/18.11 |
| 8,382,843 | B2 * | 2/2013 | Laurence et al. | 623/17.16 |
| 2006/0052870 | A1 * | 3/2006 | Ferree | 623/17.11 |
| 2006/0241770 | A1 | 10/2006 | Rhoda et al. | |
| 2009/0082868 | A1 * | 3/2009 | Cordaro et al. | 623/17.16 |

FOREIGN PATENT DOCUMENTS

| | | |
|---|---|---|
| WO | WO 99/56676 | 11/1999 |
| WO | WO 2012/051132 | 4/2012 |

* cited by examiner

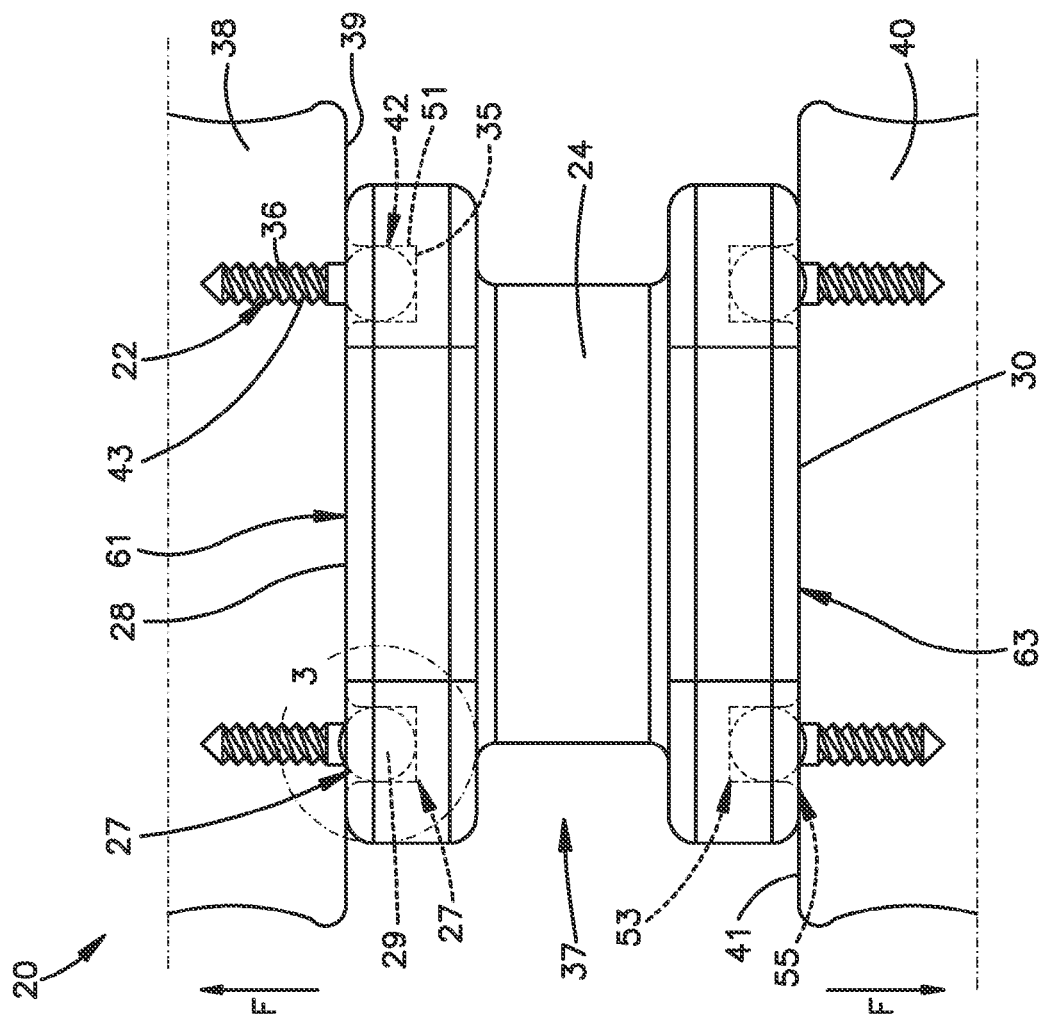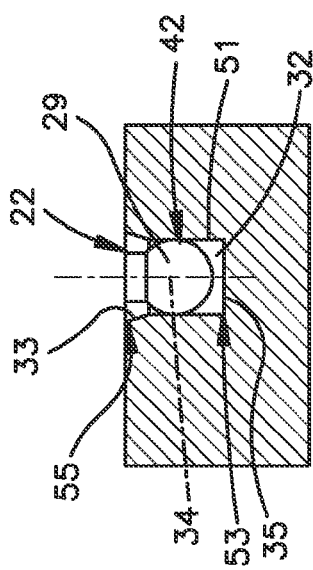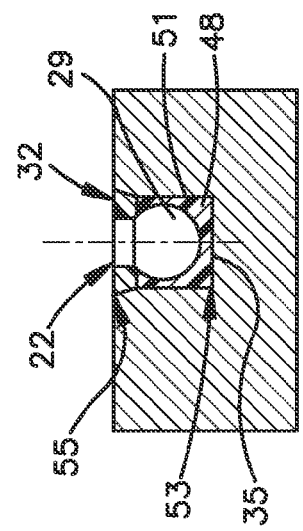

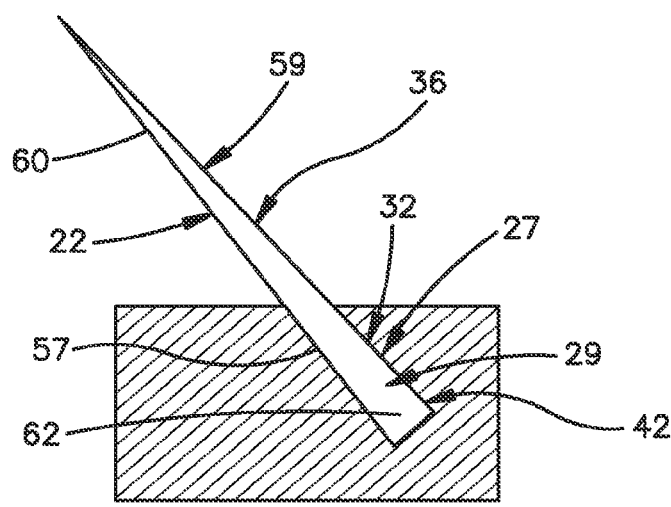
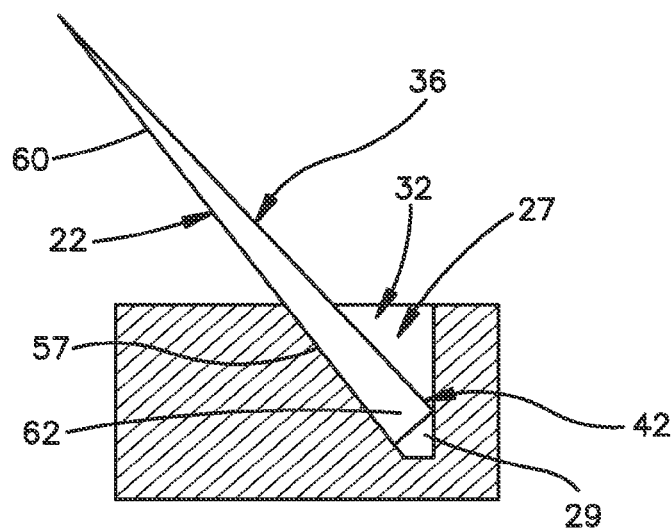
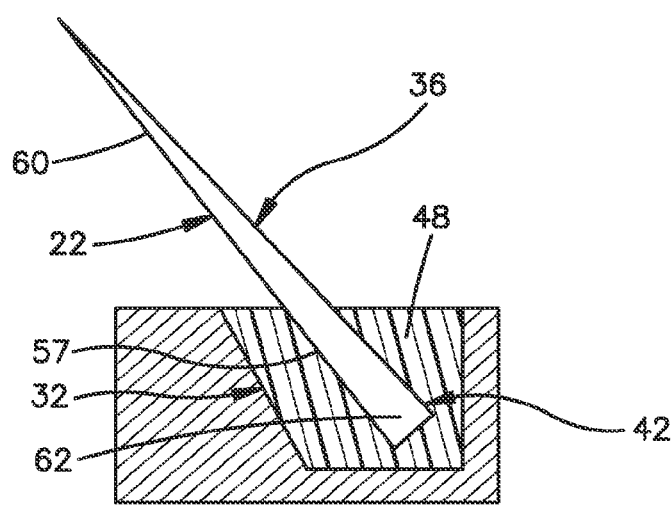

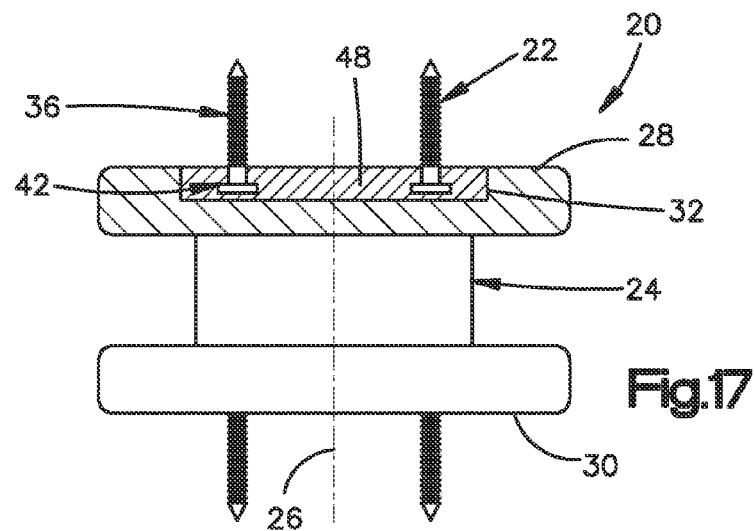
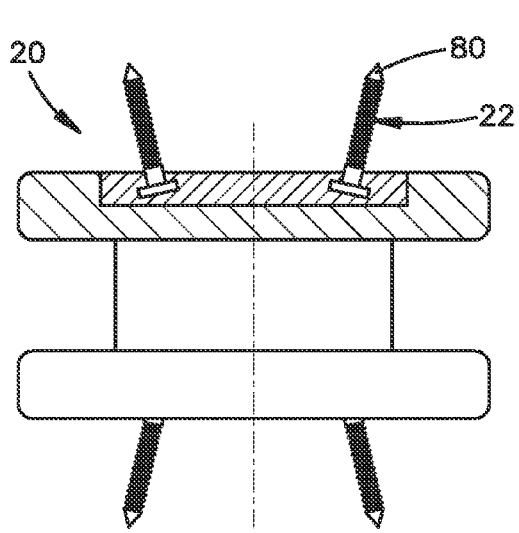 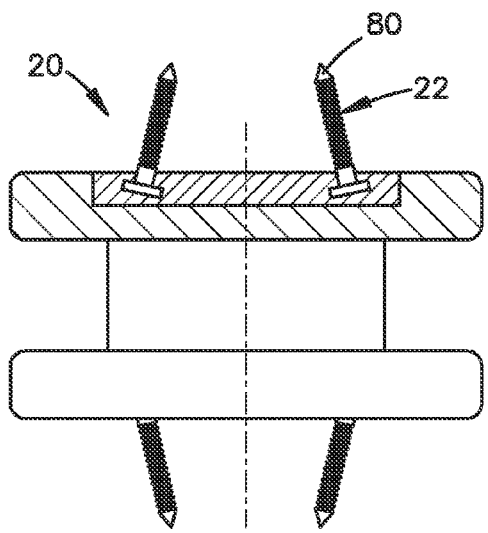
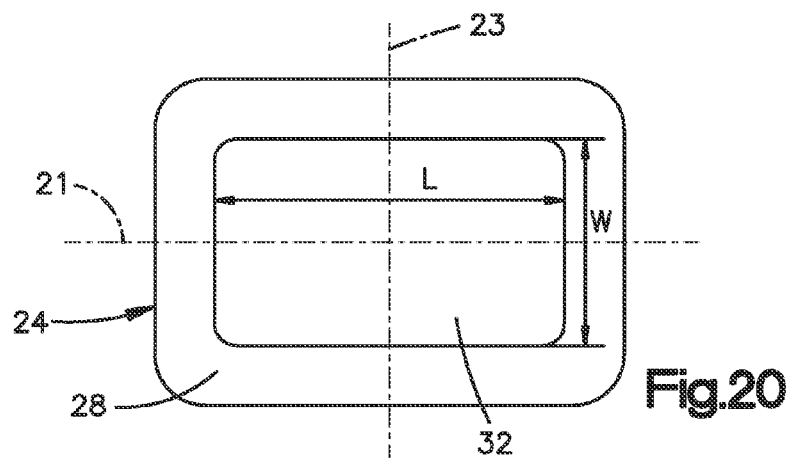

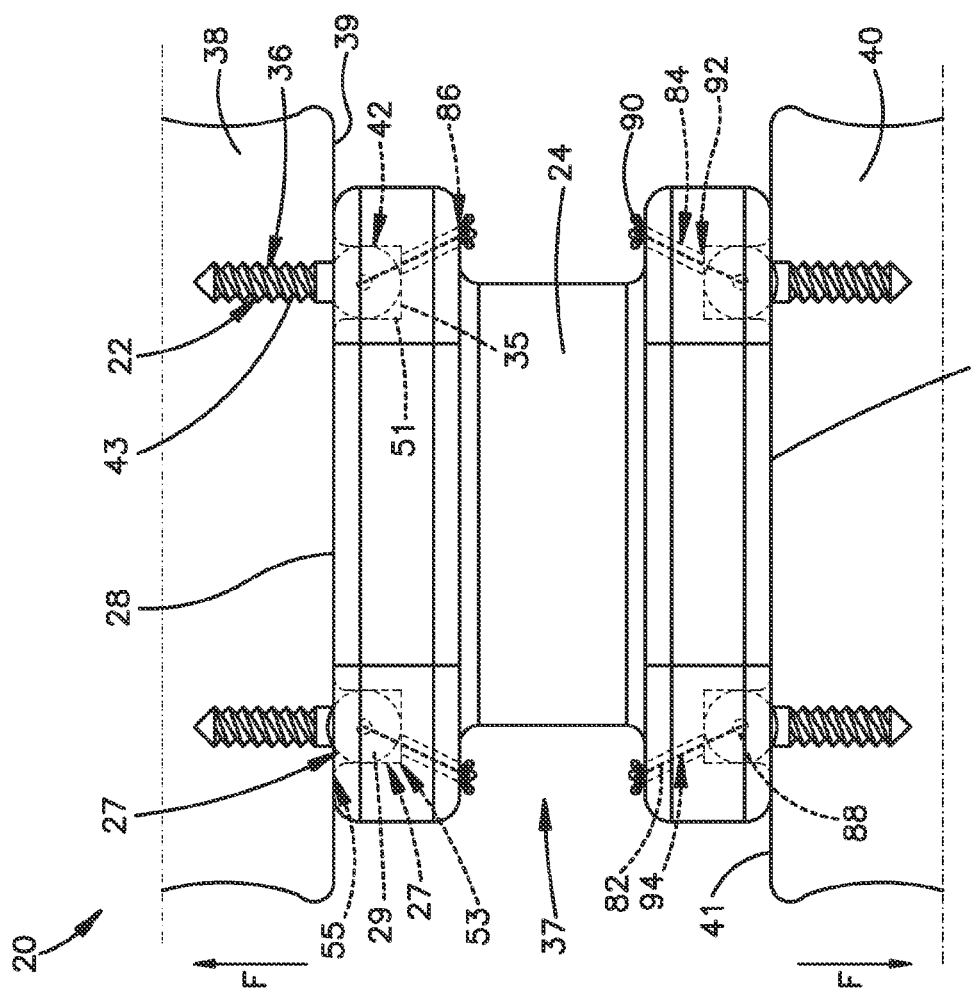

INTERVERTEBRAL IMPLANT

CROSS-REFERENCE TO RELATED APPLICATION

This patent application claims priority to, and the benefit of, U.S. provisional patent application No. 61/392,638, filed Oct. 13, 2010, the contents of which are hereby incorporated herein by reference in their entirety.

FIELD OF THE DISCLOSURE

The present disclosure generally relates to a method of fixing an intervertebral implant, and in particular relates to a method for fixing an intervertebral implant after implantation of bone anchors.

BACKGROUND

Intervertebral implants, such as spacers or total disc replacement (TDR) implants, are typically inserted into an intervertebral space disposed between the respective endplates of a pair of adjacent vertebral bodies, for instance after the disc material has been removed or to augment existing disc material. Adequate stability between intervertebral implants and the endplates of the adjacent vertebral bodies allows the implant to function properly. For instance, a poor fixation between the implant and the vertebral bodies can cause implant migration, incorrect kinematics of portions or of the entire spine and create a new source of pain for the patient.

Conventional fixation of intervertebral implants to the vertebral bodies is achieved by screwing fasteners through a portion of the implant, for instance at the anterior face of the implant, into one or two adjacent vertebral bodies. Conventional fixation can be further achieved by mechanically interlocking pointed structures, such as spikes or teeth, between the implant and the endplates of the adjacent vertebral bodies. Conventional fixation can also be achieved by inserting the intervertebral implant in the adjacent vertebral bodies. For instance, conventional intervertebral implants can include superior and inferior keels that are inserted into corresponding cut-outs formed in the adjacent vertebral bodies.

SUMMARY

In an embodiment, an implant assembly comprises an implant body defining a first bone contacting surface and a second bone contacting surface, the first bone contacting surface spaced apart from the second bone contacting surface, at least one of the first or second bone contacting surfaces defining at least one recess, such that the at least one recess is configured to receive a head of a bone anchor so that a shaft of the bone anchor extends out from the first side. The implant assembly can further include comprising the at least one bone anchor, the at least one bone anchor comprising a shaft extending from the head, the shaft configured to be inserted in a vertebral body. The at least one recess can extend into the implant body in a transverse direction. The recess can be configured as a pocket hole penetrating into the implant body from the first and second bone contact surfaces. The head can be press-fit into the at least one recess. The head can be loosely received in the at least one recess. The head can be secured to the implant body by a hardenable substance that is injected into the at least one recess. The hardenable substance can include a glue, a cement or a polymerizable monomer or copolymer. The implant assembly can further include a suture for fixing the at least one bone anchor to the at least one recess. Surfaces defining the at least one recess can be at least partially made of a shape memory material. The surfaces have an initial configuration, wherein the head fits loosely in the at least one recess, and a fixing configuration, wherein the head is tightly received within the at least one recess.

In an embodiment, the implant assembly can further include a template tht defines at least one aiming hole corresponding to the arrangement of the at least one recess of the implant body. The implant body can define a plurality of recesses, and the template comprises a plurality of aiming holes configured to be aligned with respective ones of the recesses of the implant body. The aiming holes comprise a first aiming portion and a passage connected to the aiming portion and sized greater than the aiming portion. The at least one bone anchor can defines a bore that extends along the shaft and the head. The shaft can define radial perforations in fluid communication with the bore. The first and second bone contacting surfaces can be spaced part along a central axis. The at least one bone anchor can be oriented at an oblique angle with respect to the central axis. The implant assembly can be an intervertebral implant assembly. The implant assembly can further include the at least one bone anchor configured as a staple. The staple can comprise a first pin, a second pin, and a bridge, the bridge interconnecting the first and second pins. The bridge can be press-fit inside the recess. The bridge can be loosely received within the recess. The bridge can be secured to the implant body by a hardenable substance that is injected into the recess. The recess can be sized to receive a plurality of heads. All of the plurality of heads can be secured to the implant body by a hardenable substance injected in the recess.

In an embodiment, an implant assembly includes an implant body sized to be received in an intervertebral space. The implant body defines a first bone contacting surface and a second contacting surface. The first contacting surface is spaced apart from the second contacting surface. The implant body defines a first recess extending into the first contacting surface. The first recess extends into a first side of the implant body but not through the implant body. The implant body defines a second recess extending into the second contacting surface. The second recess extends into a second side of the implant body but not through the implant body. The implant assembly further includes a first bone anchor comprising a first head and a first shaft. The first head is configured to be received inside the first recess. The first recess is configured to receive the first head of the first bone anchor so that the first shaft of the first bone anchor extends out from the first side. The implant assembly further includes a second bone anchor comprising a second head and a second shaft. The second head is configured to be received inside the second recess. The second recess is configured to receive the second head of the second bone anchor so that the second shaft of the second bone anchor extends out from the second side. The at least one of the first bone anchor or the second bone anchor is configured as a hook.

In an embodiment, a method for fixing an intervertebral implant in an intervertebral space includes the following the steps of: a) applying a spreading force to first and second vertebral bodies that define the intervertebral space so as to distract the first and second vertebral bodies; b) inserting at least one bone anchor into the first and second vertebral bodies; c) inserting an implant body into the intervertebral cavity such that an engagement member is aligned with the inserted bone anchors; and d) releasing the spreading force so that the bone anchors are secured to the engagement member of the implant body. The engagement member can comprise a recess that extends into the implant body, and the releasing step comprises the step of inserting a head of the bone anchors into the recess. The method can further include the step of injecting a hardenable substance into the recess. The at least one bone anchor can define a cannulation, and the releasing step further comprises the step of inserting a hardenable substance into the cannulation. The method can further comprise securing the bone anchor to the engagement member with a suture. The method can further include securing the bone anchor to the engagement member using a shape changing component.

In an embodiment, an implant assembly comprises an implant body defining a first bone contacting surface and a second bone contacting surface. The first bone contacting surface is spaced apart from the second bone contacting surface. The implant body comprises at least one projection extending from at least one of the first or second bone contacting surfaces in a transverse direction. The at least one projection is configured to be received in a cavity of a head of at least one bone anchor. The implant assembly can further include the at least one bone anchor. The at least one bone anchor comprises the head. The head has the cavity. The cavity is sized to receive the projection. The projection is configured to be press-fit inside the cavity. The projection can be configured to be loosely received by the cavity. The projection can secured to the at least one bone anchor in the cavity by a hardenable substance that is injected into the cavity. The hardenable substance can include a glue, a cement or a polymerizable monomer or copolymer. Surfaces defining the cavity can be at least partially made of a shape memory material, wherein the surfaces having an initial configuration, in which the projection fits loosely in the cavity, and a fixing configuration, in which the projection is tightly received within the cavity. number

BRIEF DESCRIPTION OF THE DRAWINGS

The foregoing summary, as well as the following detailed description of a preferred embodiment, are better understood when read in conjunction with the appended diagrammatic drawings. For the purpose of illustrating the invention, the drawings show an embodiment that is presently preferred. The invention is not limited, however, to the specific instrumentalities disclosed in the drawings. In the drawings:

FIG. 2 is a side elevation view of the intervertebral implant illustrated in FIG. 1;

FIG. 3 is an enlarged view of Region 3 illustrated in FIG. 2 showing an alternate version of a recess;

FIG. 4 is an enlarged view of a portion of an intervertebral implant similar to Region 3 of FIG. 2, but constructed in accordance with another embodiment;

FIG. 9 illustrates a magnified view of Region 9 illustrated in FIG. 8;

FIG. 10 is an enlarged view of a portion of an intervertebral implant similar to Region 9 of FIG. 8, but constructed in accordance with another embodiment;

FIG. 11 is an enlarged view of a portion of an intervertebral implant similar to Region 9 of FIG. 8, but constructed in accordance with another embodiment;

FIGS. 17 to 19 are side elevation views showing partial cross sections of an intervertebral implant constructed in accordance with another embodiment;

FIG. 20 is a top plan view of the intervertebral implant illustrated in FIGS. 17-19; and FIG. 21 is a side elevation view of an intervertebral implant constructed in accordance with another embodiment.

DETAILED DESCRIPTION

Figure 1:
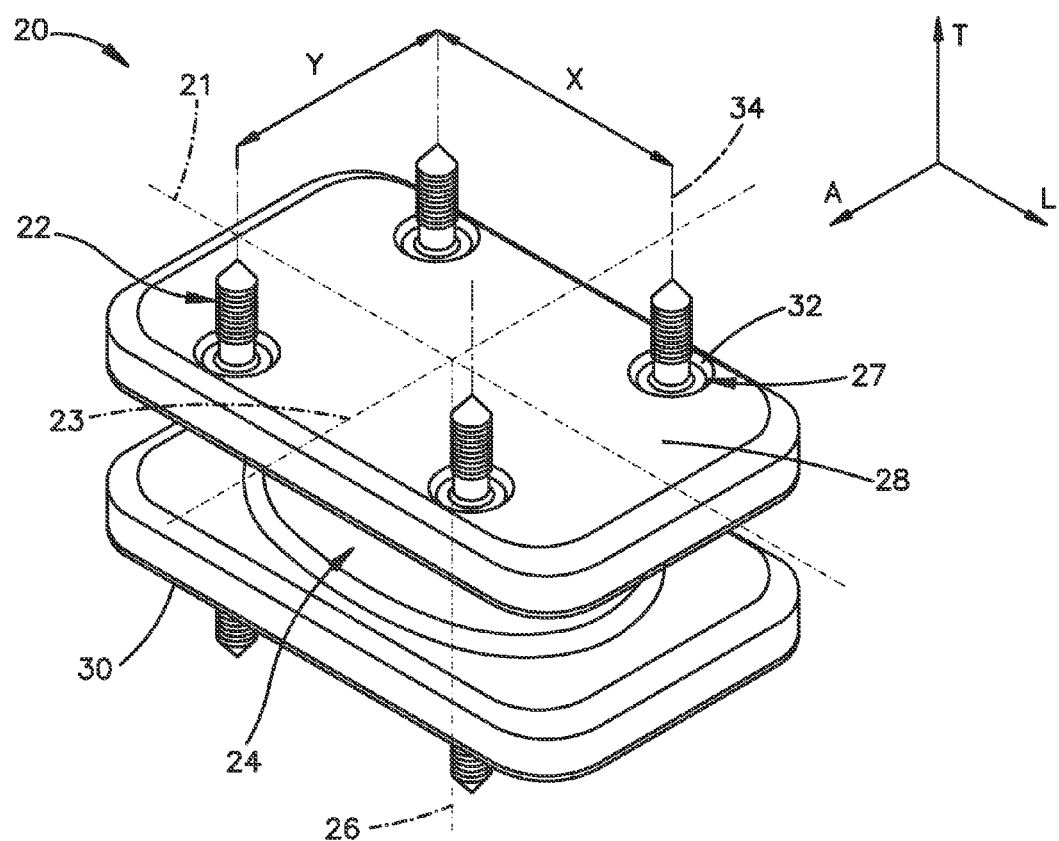
FIG. 1 is a perspective view of an intervertebral implant constructed in accordance with one embodiment.

Referring to FIGS. 1-3, an intervertebral implant 20, which can be used a total disc replacement, a spacer, a corpectomy device, or any other apparatus suitable for implantation in an intervertebral space, includes an implant body 24 and at least one bone anchor 22, such as a number of bone anchors 22, configured to fix the implant body 24 in an intervertebral space 37 defined by a first superior vertebral body 38 and a second vertebral body 40 that present respective first and second vertebral endplates 39 and 41. In accordance with the illustrated embodiment, the implant 20 includes eight bone anchors 22; however, any number of bone anchors 22 could be used as desired. The bone anchors 22 can be made from a metal, polymer or any reinforced polymer such as a fiber reinforced polymer. In addition, the bone anchors 22 can be made of a biodegradable material like surface treated Mg or Iron-based alloys.

The implant body 24 defines a first bone contacting surface 28 and an opposed second bone contacting surface 30 that is spaced from the first bone contacting surface 28 along a central axis 26 that extends along a transverse direction T. The first and second bone contacting surfaces 28 and 30 can extend substantially in respective planes that are substantially orthogonal to the central axis 26. The first and second bone contacting surfaces 28 and 30 can define a substantially rectangular shape in a cross-section orthogonal to the central axis 26, a center of which can lie on the central axis 26. It should be appreciated that the implant body 24 and bone contacting surfaces 28 and 30 can have any alternative shape as desired. For example, either the first bone contacting surface 28 or the second contacting surface 30 can have a substantially circular or oval shape in a cross-section orthogonal to the central axis 26. The implant body 24 defines a longitudinal axis 21 extending along a longitudinal direction L that is orthogonal to the transverse direction T, and a lateral axis 23 that extends along a lateral direction A that is orthogonal to the transverse and longitudinal directions T and L. In accordance with the illustrated embodiment, the transverse direction T is oriented vertically, and the longitudinal and lateral directions L and A are oriented horizontally, though it should be appreciated that the orientation of the implant 20 may vary during use. As illustrated, the implant body 24 defines a longitudinal length, a lateral width, and a transverse height.

The implant 20 can define at least one engagement member 27 in the form of a recess 32, such as a number of recesses 32, that extend transversely into the first bone contacting surface 28. The implant 20 can further define at least one recess 32, such as a number of recesses 32, that extend transversely into the second bone contacting surface 30. In accordance with the illustrated embodiment, the implant 20 defines an equal number (e.g., four) of recesses 32 that extend into the bone contacting surfaces 28 and 30. The recesses 32 can be configured as pockets that each extends along a respective hole axis 34. In accordance with the illustrated embodiment, the recesses 32 are disposed proximate to the corners of the bone contacting surfaces 28 and 30. The recesses 32 in the first and second bone contacting surfaces 28, 30 of the implant body 24 are arranged in such a way that their hole axes 34 are spaced apart by a longitudinal distance X and by a lateral distance Y.

The bone anchors 22 include a first portion in the form of a shaft 36 that is configured to be anchored in the respective endplates 39 and 41, and a second portion in the form of a head 42 that extends, either directly or indirectly, from the shaft 36 and is configured to fit into the recesses 32 so as to secure the vertebral body 24 to the first and second vertebral bodies 38 and 40. The head 42 can be inline with the shaft 36, and can define a cross-sectional dimension greater or less than that of the shaft 36 (greater as illustrated), or can define substantially the same shape as the shaft 36. The bone anchor shafts 36 of the bone anchors 22 can be provided as screws that define external threading 43 and can be self-drilling and self-tapping. Each bone anchor 22 can engage one recess 32 so as to attach the bone anchor 22 to the intervertebral implant 20. At least one recess 32 extends into a first side 61 of the implant body 24 but not through the implant body 24, such that the recess 32 is configured to receive the head 42 of a bone anchor 22 so that the shaft 36 of the bone anchor 22 extends out from the first side 61. At least one recess 32 extens into a second side 63 of the implant body 24 but not through the implant body 24, such that the recess 32 is configured to receive the head 42 of a bone anchor 22 so that the shaft 36 of the bone anchor 22 extends out from the second side 63.

With continued reference to FIGS. 1-3, in one embodiment, the intervertebral implant 20 includes the implant body 24 defining a central axis 26. The implant body 24 includes the first bone contacting surface 28, which can be arranged transversely to the central axis 26, and the second bone contacting surface 30, which can be arranged transversely to the central axis 26. Aside from the first and second bone contacting surfaces 28 and 30, the implant body 24 can further include a number of recesses 32 in the first bone contacting surface 28 and/or a number of recesses 32 in the second bone contacting surface 30. The intervertebral implant 20 can further include a number of bone anchors 22 each configured to be anchored to a bone. Each of the bone anchors 22 can have the shaft 36 configured to be anchored in a bone and the head 42 configured and sized to be received within at least one of the recesses 32. The heads 42 of the bone anchors 22 that are configured to be anchored to the first vertebral body 38 are configured and sized to be placed within at least one the recesses 32 located in the first bone contacting surface 28. The heads 42 of the bone anchors 22 that are configured to be anchored to the second vertebral body 40 are configured and sized to be placed within at least one the recesses 32 located in the second bone contacting surface 30 of the implant body 24. In an embodiment, the intervertebral implant 20 can comprise a number of bone anchors 22, and the implant body 24 can comprise a number of recesses 32 in the first bone contacting surface 28 and a number of recesses 32 in the second bone contacting surface 30.

With continued reference to FIGS. 1-3, in an embodiment, the recesses 32 can be configured as pocket holes penetrating into the implant body 24 from the first and/or second bone contacting surface 28, 30. The bone anchors 22 can be fixable in a stable manner in the recesses 32. Each recess 32 can be defined by surfaces of the implant body 24. For instance, in the depicted embodiment, each recess 32 is defined by a bottom surface 35 and an enclosed lateral surface 51. The enclosed lateral surface 51 can have an annular configuration and can be oriented substantially orthogonal to the first or second bone contacting surface 28 or 30. The bottom surface 35 can be substantially parallel to the first or second bone contacting surface 28 or 32.

FIGS. 2 and 3 show variants of suitable recesses 32. For instance, the recess shown in FIG. 3 is deeper than the recess shown in FIG. 2. The recesses can operate in substantially the same manner; however, the position of the bone anchor 22 inside the recess is different in FIG. 3 than in FIG. 2. For instance, in the recess shown in FIG. 2, the bone anchor 22 abuts the bottom surface 35 partially defining the recess 32. Hence, when the head 42 of the bone anchor 22 is positioned within the recess 32, there is no clearance between the head 42 of the bone anchor 22 and the bottom surface 35 partially defining the recess 32. In addition, when the head 42 of the bone anchor 22 is positioned within the recess 32, there is no clearance between the head 42 and the enclosed lateral surface 51.

In the recess shown in FIG. 3, the bone anchor 22 is retained above the bottom surface 35 partially defining the recess 32, thereby allowing limited axial movement of the bone anchor 22 along the hole axis 34. Thus, the bottom surface 35 does not necessarily contact the head 42 of the bone anchor 22. Referring to FIG. 3, the recess 32 can define respective beveled or conical lead-in sections 33 at their openings so as to facilitate insertion of the anchor heads 42. In this regard, the head 42 can also be referred to as an engagement member 29 that is configured to engage the engagement member 27 of the implant body 24 so as to secure the bone anchors 22 to the implant body 24. The recesses 32 can have a depth along the transverse direction T between a first end 53 and a lower end 55 of the recess 32. In the embodiment shown in FIG. 3, the depth of the recess 32 along the transverse direction T is greater than the length of the bone anchor heads 42 along the transverse direction T when the bone anchors 22 are transversely oriented. However, the depth of the recess 32 along the transverse direction T can alternatively be substantially equal to or less than the length of the bone anchor heads 42 along the transverse direction T as shown in FIG. 2.

The anchor heads 42 are illustrated as spherical in shape and sized to snugly fit, or be press-fit, into the recesses 32. For instance, the spherical anchor heads 42 can have a diameter that is substantially equal to the diameter of the recesses 32, though it should be appreciated that the anchor heads 42 can define any suitable size and shape as desired. The anchor heads 42 can be shaped differently than the anchor shafts 36 such that only the anchor heads 42 are configured to mechanically connect to the implant body 24. Accordingly, the bone anchors 22 can define a uni-directional plug-in connection between the heads 42 and the recesses 32 formed in the implant body 24. Thus, in this embodiment, the heads 42 of the bone anchors 22 can be mechanically connectable to the recesses 32 only via a plug-in connection, wherein the heads 42 are inserted in the recesses 32. As used herein, the term "plug-in connection" refers to a connection where the head 42 is positioned inside the recess 32. The plug-in connection can be a uni-directional or an omni-directional plug-in connection. In a uni-directional plug-in connection, the head 42 can move in only one direction relative to the recess 32. For example, as shown in FIG. 3, the head 42 can move only axially along the transverse direction T but cannot move in any other direction when positioned in the recess 32. As shown in FIG. 3, the enclosed lateral wall 51 contacts the head 42, preventing the head 42 from moving in the longitudinal direction L and in the lateral direction A when the head 42 is inserted in the recess 32. The heads 42 of the bone anchors 22 can be removably positioned within the recesses 32 via a unidirectional plug-in connection. In an omni-directional plug-in connection, the head 42 can move in more than one direction when inserted in the recess 32. In an omni-directional plug-in connection, the head 42 positioned inside the recess 32 can move, for instance, along the transverse direction T and along the longitudinal direction L. Alternatively, in an omni-directional plug-in connection, the head 42 positioned inside the recess 32 can move along the transverse direction T, along the longitudinal direction T, and along the lateral direction A.

In accordance with one embodiment, the intervertebral implant 20 can be inserted into the intervertebral space 37 by performing the following steps. First, a transverse spreading force F can be applied to the first and second vertebral bodies 38 and 40, so as to distract the vertebral bodies 38 and 40. The intervertebral disc disposed in the intervertebral space 37 can be removed. The bone anchors 22 can then be secured to the vertebral bodies 38 and 40, for instance by inserting (threadedly inserting as illustrated) the anchor shafts 36 into the respective vertebral endplates 39 and 41. Thus, at least one bone anchor 22, such as a first number of bone anchors 22, are fixed to the first vertebral body 38, and another at least one such as a number of bone anchors 22 are fixed to the second vertebral body 40. As described in more detail below with reference to FIGS. 14-16, a template 44 can accurately position the bone anchors 22 in the respective vertebral bodies 38 and 40.

After fixing the bone anchors 22 in the first and second vertebral bodies 38 and 40, the implant body 24 is inserted into the intervertebral space 37, and the recesses 32 of the implant body 24 are aligned with the previously set bone anchors 22. For instance, the recesses 32 that extend into the superior bone contacting surface 28 are aligned with the bone anchors 22 that have been driven into the superior vertebral body 38, and the recesses 32 that extend into the inferior bone contacting surface 30 are aligned with the bone anchors 22 that have been driven into the inferior vertebral body 40. The spreading force F can then be released, which causes the vertebral bodies 38 and 40 to anatomically compress toward each other, thereby causing the recesses 32 to receive the respective bone anchor heads 42. Because the anchor heads 42 are form-fitted in the recesses 32, the anchor heads 42 are restricted with respect to lateral and longitudinal movement relative to the vertebral bodies 38 and 40 in at least one of or both of the lateral and longitudinal directions. In other words, in this embodiment, the bone anchors 22 are held form-fittingly in the recesses 32. As a result, the heads 42 are laterally retained in the recesses 32 to prevent a lateral movement of the implant body 24 relative to the vertebral bodies 38 and 40.

Referring to FIG. 2, one method for fixation of an intervertebral implant comprises the following steps: (a) applying a spreading force F to the first and second adjacent vertebral bodies 38 and 40; (b) removing the intervertebral disc between the adjacent first and second vertebral bodies 38 and 40; (c) setting one or more bone anchors 22 in the natural endplate 39, 41 of one or each of the first and/or second vertebral bodies 38, 40 before inserting an intervertebral body 24 having a number of recesses 32 or projections 64 (FIG. 12) in or on the first bone contacting surface 28 and/or a number of recesses 32 or projections 64 (FIG. 12) in or on the second bone contacting surface 30 between the adjacent first and second vertebral bodies 38, 40; (d) inserting the implant body 24 into the intervertebral cavity 37 and aligning the recesses 32 or the projections 64 of the implant body 24 with the previously set bone anchors 22; and (e) releasing the spreading force F so that the head 42 of each of the one or more bone anchors 22 in one or each of the first and second vertebral body 38, 40 is connected to one of the number of recesses 32 or projections 64 in the first and/or second bone contacting surface 28, 30.

With continued reference to FIG. 2, another method for fixing an intervertebral implant in an intervertebral space can include the following steps: (1) positioning and inserting the bone anchors 22 in the endplates 39, 41 of two adjacent vertebrae 38 and 40; and (2) inserting the implant 20 into the intervertebral space 37 and engaging the implant 20 with the bone anchors 22. The implant can be inserted into the intervertebral space 37 along any suitable surgical access path, such as an anterior access or a lateral access. The implant 20 can achieve reliable primary stability. The bone anchors 22 are implanted directly into the vertebral bodies 38 and 40 prior to the insertion of the implant 20, thereby reducing or eliminating the occurrence of damage to the endplates 39 and 41. The number of bone anchors 22 to be implanted can be selected by the surgeon. Therefore, the surgeon can intraoperatively improve the primary fixation as desired. The implant 20 can be subsequently inserted between the two adjacent vertebral bodies 38, 40 and brought into engagement with the implanted bone anchors 22 to be locked in its position.

The implant 20 can be removed from the bone anchors 22 as desired in order to select an implant 20 with another size, height, length, width or lordosis or in case of a revision procedure. A total disc replacement implant could e.g. be replaced by an implant with a similar bone anchor engagement pattern without removing the bone anchors. The position/direction of the bone anchors 22, which can be screws, can be adjusted as desired, such that any anatomically desired bone anchor position/direction can be chosen for fixation of the implant. The surgeon can also determine the desired depth to which the bone anchor 22 is inserted into the vertebral body 38 or 40 for fixation of the implant 20. One or more bone anchors 22 (e.g., four bone anchors) can be set in each of the first and second vertebral bodies 38 and 40. The number of recesses 32 formed in each bone contacting surface 28, 30 can be between one and four, so that each one bone anchor 22 engages with one recess 32. The number of recesses 32 in the first bone contacting surface 28 can differ from the number of recesses 32 in the second bone contacting surface 30, and vice-versa.

One or more up to all of the anchor heads 42 can be substantially spherical as illustrated, thereby facilitating the insertion of the anchor heads 42 into the recesses in any orientation. Alternatively, one or more up to all of the anchor heads 42 and the recesses 32 can be polygonal such that the anchor heads 42 fit into the recesses 32 when the anchor heads 42 are at a predetermined angular orientation. The polygonal shape of the anchor heads 42 can interfere with the polygonal shape of the recesses 32 so as to prevent the anchor heads 42 from rotating in the recesses 32 about the hole axis 34 or an axis that is orthogonal to the hole axis 34.

Alternatively still, referring to FIG. 4, one or more up to all of the anchor heads 42 can be sized smaller than the recesses 32 in one or both of the lateral and longitudinal directions, such that the anchor heads 42 are loosely received in the recesses 32 in one or both of the longitudinal and lateral directions. A hardenable substance 48, such preferably a glue, a cement or a polymerizable monomer or comonomer, or any suitable alternative fastener, can then be inserted or injected into the recesses 32 so as to fasten the loosely received portion or entirety of the anchor head 42 to the implant body 24 inside the recesses 32. In other words, the bone anchors 22 can fit loosely within the recesses 32 so that, after completing the insertion of the intervertebral implant 20, the bone anchors 22 can be glued or otherwise fixed in place to the implant body 24 by the surgeon. The bone anchors 22 can be attached to the bone contacting surface 28 or 30 with an adhesive made of any polymer based glue, such as a polyurethane-based or fibrin glue. Any of the methods for fixing an implant described herein can further comprise the step of injecting the hardenable substance 48, preferably a glue, a cement or a polymerizable monomer or comonomer into the recesses 32, thereby securely locking the implant 20 in position with respect to the two adjacent vertebral bodies 38 and 40 after the bone anchors 22 have been inserted into the recess 32 during implantation of the intervertebral implant 20. Thus, the heads 42 of the bone anchors 22 can be connectable to the recesses 32 via the hardenable substance 48, which can be, for example, glue, cement or a polymerizable monomer or comonomer.

While the bone anchors 22 have been illustrated as screws as described above, it should be appreciated that the bone anchors 22 can be provided as nails, pins, screws, hooks, staples, or any suitable alternatively constructed bone fixation member as desired. For instance, referring now to FIGS. 5-6, the intervertebral implant 20 can be constructed such that the bone anchors 22 are configured as hooks 52 each having a shaft 36 that can be configured as a substantially straight pin or nail that can be pressed into the vertebral endplates 39 and 41 of the vertebral bodies 38 and 40. In particular, the shafts 36 can be pressed directly into the vertebral bodies 38 and 40, or a hole can be pre-formed in the vertebral bodies and the shafts 36 can be pressed into the pre-formed holes. Thus, it should be appreciated that the shaft 36 can be unthreaded.

The heads 42 of the hooks 52 can be angularly offset with respect to the shaft 36, and can be bent so as to define one or more elbows 45, or can extend substantially straight or can be curved or otherwise shaped as desired. In accordance with the illustrated embodiment, the heads 42 include a proximal head portion 42a that extends from the shaft 36 and is angularly offset with respect to the shaft 36, and a distal head portion 42b that is angularly offset with respect to the proximal head portion 42a and separated by the proximal head portion 42a by the elbow 45.

Figure 5:
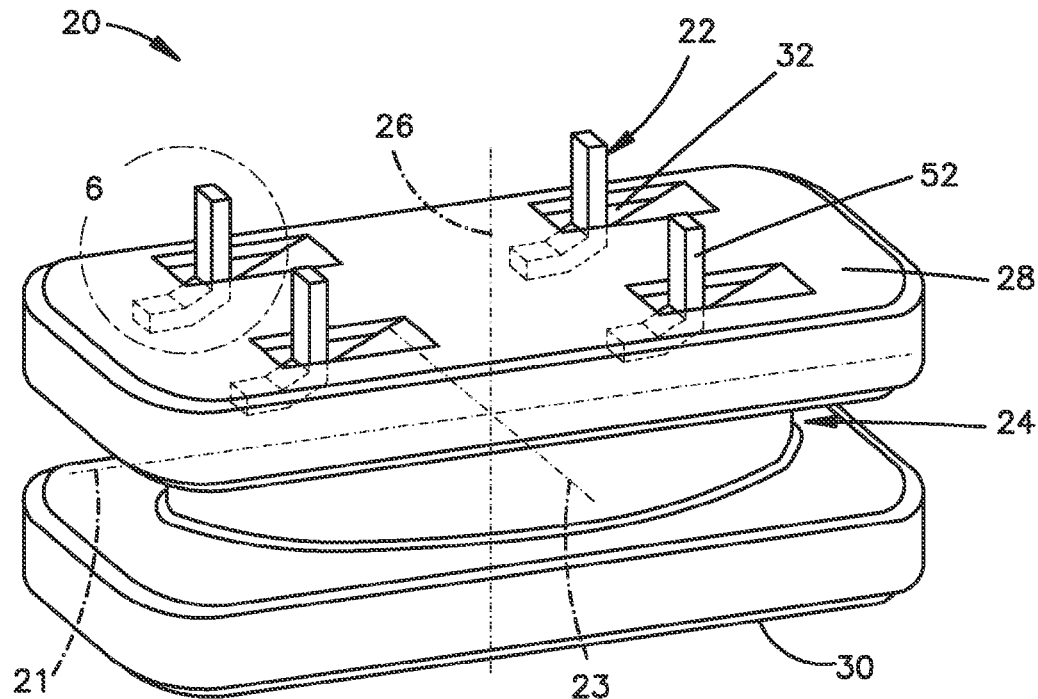
FIG. 5 is a perspective view of an intervertebral implant constructed in accordance with another embodiment.
Figure 6:
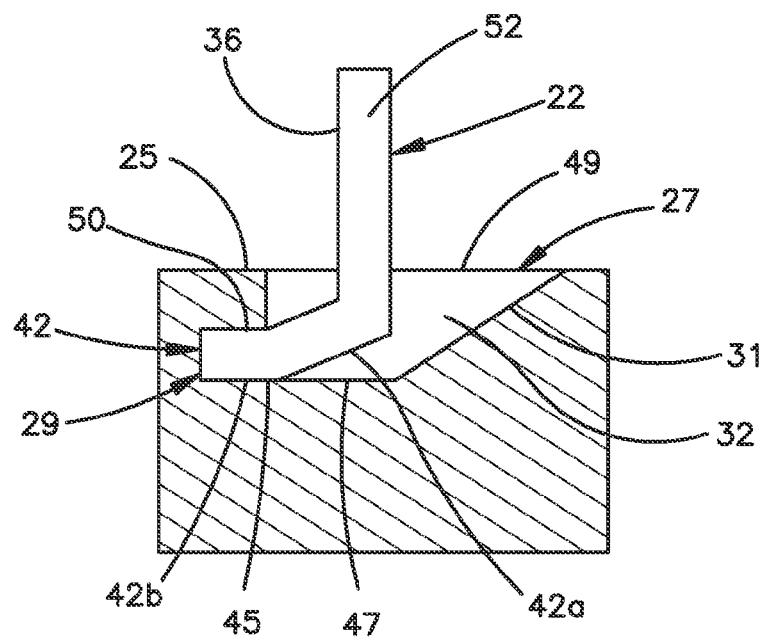
FIG. 6 is an enlarged view of Region 6 illustrated in FIG. 5.

With continuing reference to FIGS. 5-6, the implant body 24 defines beveled lead-in surface 31 that is connected to a substantially horizontal base 47 of each recess 32 that defines a mouth 49 of the recess 32. Each recess 32 can further include an undercut 50 that extends longitudinally into the implant body 24 from the mouth 49, such that the implant body 32 defines an overhang 25 that extends over the undercut 50. The undercut 50 is sized substantially equal to the distal portion 42b of the hook 52.

During operation, the vertebral bodies 38 and 40 can be spread apart, and intervertebral disc material can be removed, and the shafts 36 of the hooks 52 can be inserted into the vertebral bodies 38 and 40 in the manner described above. The implant body 24 can then be positioned such that the heads 42 of the hooks are aligned with the mouths 49 of the respective recesses 32, and the heads 42 can be inserted into the recess 32 in a transverse direction and subsequently inserted into the undercuts 50 by longitudinally displacing the implant body 24. Alternatively, the anchor heads 42 can be installed in the implant body 24 prior to inserting the anchor shafts 36 into the vertebral bodies 38 and 40.

The distal head portions 42b can have a cross-sectional dimension substantially equal to that of the undercuts 50 so that the distal head portions 42b form-fittingly engage with the respective recesses 32. Alternatively, the heads 42, for instance the distal head portions 42b, can be sized less than the recess, for instance at the undercut 50, and thus configured to be loosely received in the recesses 32. A hardenable substance 48 can be injected into the recesses 32 so as to fix the anchor heads 42 to the implant body 24 inside the recesses 32. Alternatively or additionally, any suitable mechanical fastener can fix the anchors 22 to the implant 24.

Figure 7:
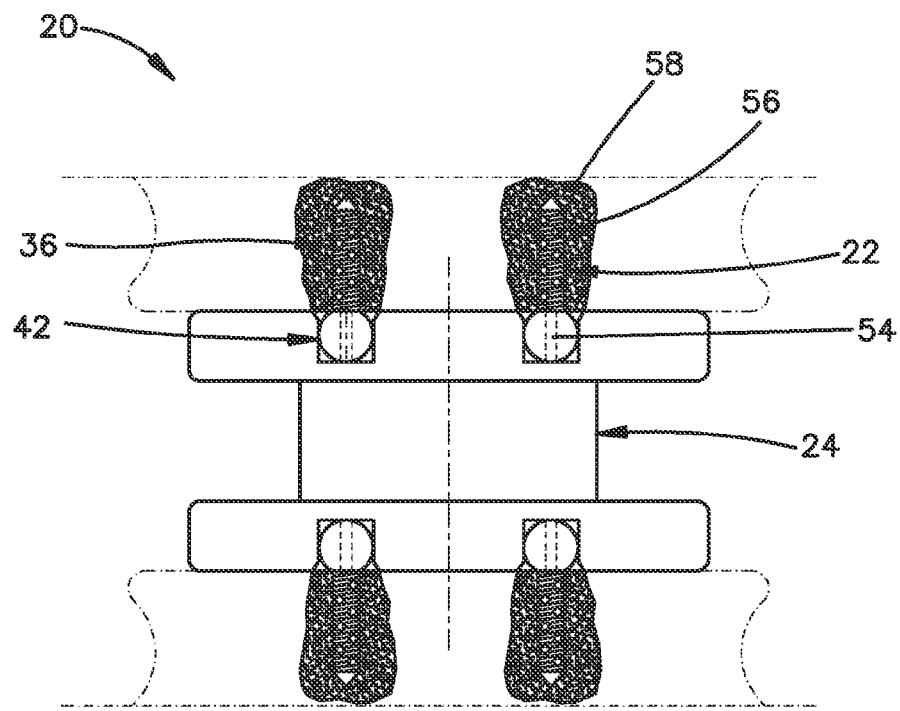
FIG. 7 is a side elevation view of an intervertebral implant constructed in accordance with another embodiment.
Figure 8:
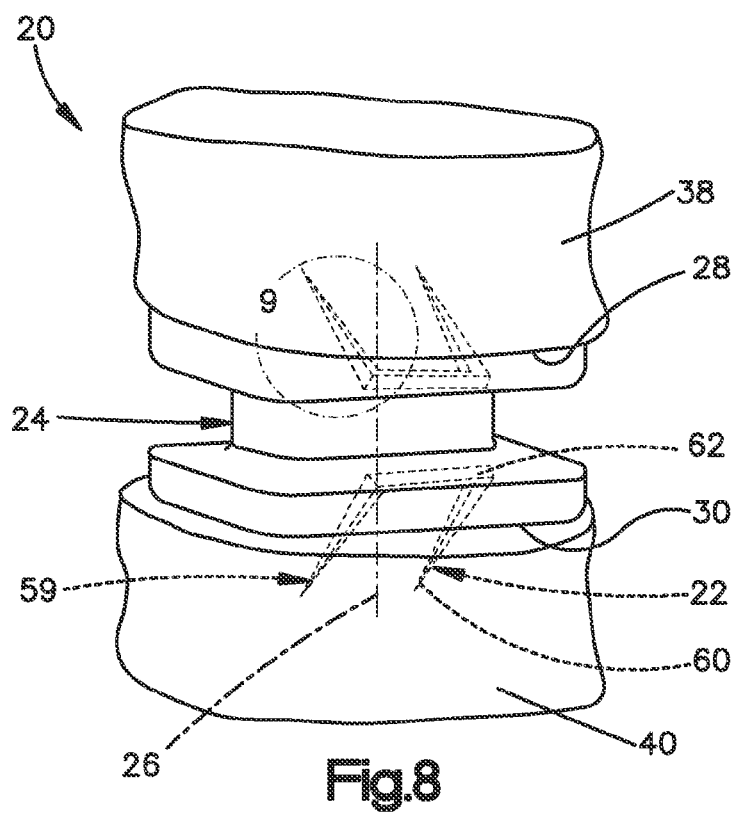
FIG. 8 is a perspective view of an intervertebral implant constructed in accordance with another embodiment.

Referring now to FIG. 7, the bone anchors 22 of the intervertebral implant 20 can include a cannulation or bore 54 that extends along the shaft axis, and can extend through or into the shaft 36, and additionally or alternatively can extend through or into the head 42. The bone anchors 22 can further include at least one radial perforation 56 such as a number of radial perforations 56 that extend into the shaft 36 and/or head 42 to a depth such that the radial perforations 56 are in fluid communication with the cannulation 54. In accordance with the illustrated embodiment, the cannulations 54 can define an opening at the terminal end of the shaft 36, and can extend into the anchor head 42. Thus, a bone cement 58, or any other suitable hardenable substance, can be injected through the cannulation 54 and the radial perforations 56 into the bone tissue surrounding the bone anchor 22. The bone anchors 22 can be cannulated and can comprise radial perforations 56. Thus, a bone cement can be injected through the cannulation 54 and the radial perforations 56 into the surrounding bone. Any of the exemplary methods for fixing an implant described above can further include the step of injecting bone cement 58, or any other suitable hardenable substance, through cannulated and perforated bone anchors 22, thereby securely locking the implant 20 in a desired position with respect to the two adjacent vertebral bodies 38 and 40.

Referring now to FIGS. 8-11, the bone anchors 22 can alternatively be configured as staples 59. In accordance with the illustrated embodiment, the intervertebral implant 20 can include at least one staple 59 extending from each of the bone contacting surfaces 28 and 30, and a corresponding at least one recess 32 that extends into the implant body 24 from the bone contacting surfaces 28 and 30. A first portion of the bone anchors 22 (e.g., staples 59) is configured to be disposed in the recess 32, while a second portion of the bone anchors 22 is configured to be fixed to the vertebral bodies 38 and 40.

Each staple 59 includes a pair of spaced legs in the form of pins 60 that provide the anchor shaft 36, and a bridge 62 that is connected between the two pins 60 and provides the anchor head 42. In one embodiment, each staple 59 comprises two substantially parallel pins 60 that are configured to be anchored to bone. The pins 60 are thus configured to extend into the vertebral bodies 38 and 40 so as to fix the staples 59 to the vertebral bodies, and the bridge 62 is configured to be disposed in the recess 32 so as to be connected to the implant body 24. The pins 60 can be tapered toward their distal ends along a direction away from the bridge 62.

As illustrated in FIG. 9, the bridge 62 of each bone anchor 22 can be sized substantially equal with the respective recesses such that the bridge 62 is press-fit inside the recess 32. The bridge 62 can be inserted into the recesses 32 along a direction oblique to the central transverse axis 26 of the implant body 24. Alternatively, as illustrated in FIG. 10, the bridge 62 can be sized smaller than the recess such that the bridge 62 is loosely received in the recess 32. The bone anchors 22 can be configured as staples 59 forming an oblique unidirectional plug-in connection to prevent the implant from migrating in the intervertebral space. In the oblique unidirectional plug-in connection, the bridge 62 in inserted inside the recesses 32 at an oblique angle relative to the central axis 26. Moreover, in this oblique unidirectional plug-in connection, the bridge 26 can move only in one direction (i.e., at the oblique angle with respect to the central axis 26. To achieve the oblique unidirectional plug-in connection, the implant body 24 can include at least one angled lateral surface 57 partially defining the recess 32. The angled lateral surface 57 is oriented at an oblique angle relative to the central axis 26 and/or the bone contacting surfaces 28 or 30. The bridge 62 can be inserted into the recesses 32 in a direction along the central axis 26 of the implant body 24. Referring to FIG. 11, the recess 32 can be sized larger than the bridge 62 of the bone anchor 22. The bridging portions 62 can be inserted into the recesses 32 in a direction along the central axis 26 of the implant body 24 or oblique to the central axis 26. Furthermore, the second anchor heads 42 can be fixed to the anchor body 24 inside the recesses 32 using a hardenable substance 48 that can be injected into the recesses 32.

Figure 12:
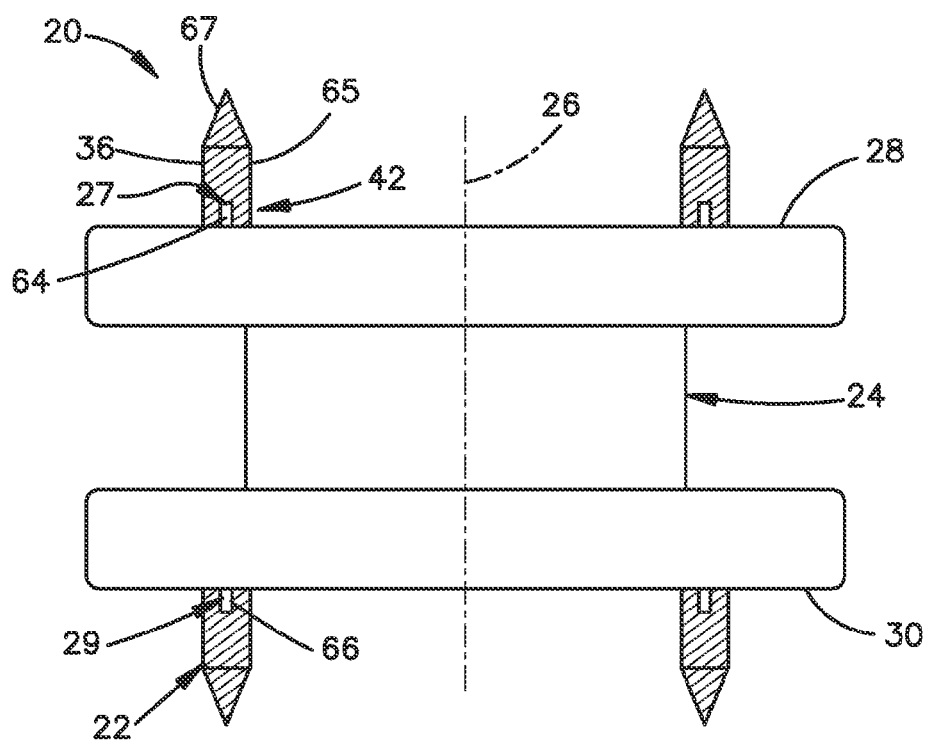
FIG. 12 is a side elevation view of an intervertebral implant constructed in accordance with another embodiment.
Figure 13:
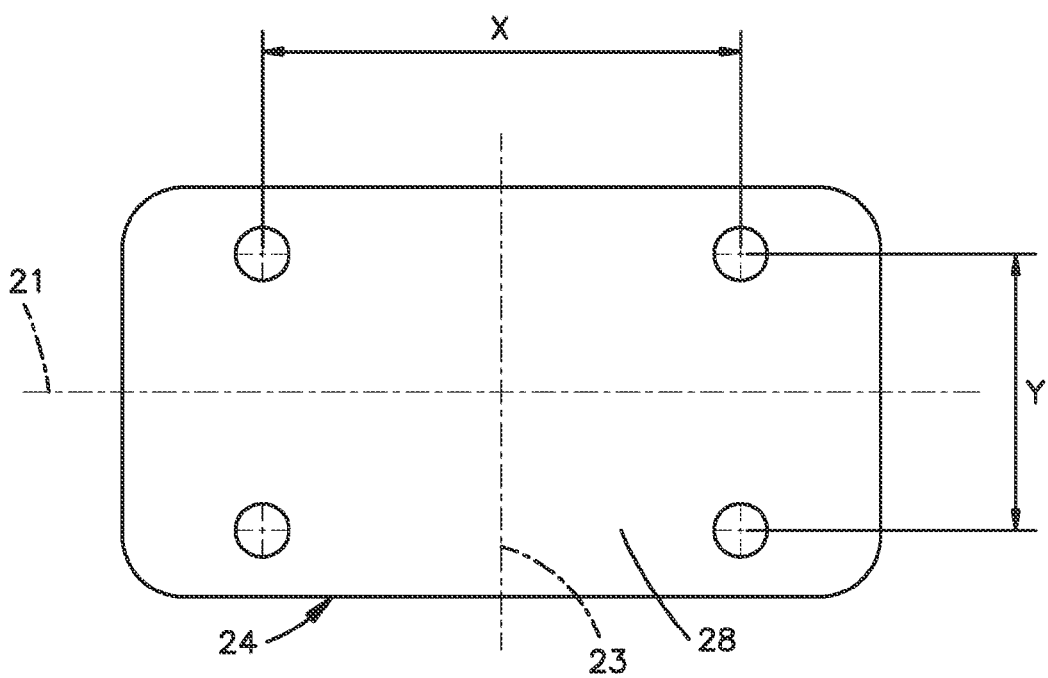
FIG. 13 is a top plan view of the intervertebral implant illustrated in FIG. 12.

Referring to FIGS. 12-13, the bone anchors 22 of the intervertebral implant 20 can be configured as pins 65 that each defines a head 42 configured to engage the implant body 24 so as to fix the pin 65 to the implant body 24, and a shaft 36 configured to be fixed to the vertebral bodies 38 and 40. The shaft 36 can include a tapered distal tip 67 configured to facilitate insertion into the vertebral bodies 38 and 40. The tapered distal tips 67 can have a substantially frusto-conical shape or any other suitable shape. Each bone anchor 22 can include a cavity 66 that extends into the head 42. The cavities 66 can be cylindrical or any alternative shape as desired.

The implant body 24 includes a number of engagement members 27 in the form of projections 64 that extend out from the first bone contacting surface 28 and the second bone contacting surface 30. The projections 64 are configured to engage complementary engagement members 29 of the bone anchors 22 provided as the heads 42, and in particular the cavities 66 formed into the heads 42. The number of projections 64 that extend from each bone contacting surface 28, 30 can be between one and four, such that each one bone anchor engages with one projection 64. The number of projections 64 of the first bone contacting surface 28 can differ from the number of projections 64 of the second bone contacting surface 30, and vice-versa.

During operation, the shafts 36 of the bone anchors 22, which can be cylindrically shaped or alternatively shaped as desired, can be pressed or hammered into the endplates 39 and 41 of the vertebral bodies 38 and 40. The projections 64 and cavities 66 can be substantially equally sized such that the projections 64 are press-fit inside the cavities 66. Alternatively, the cavities 66 can be sized greater than the projections 64, and an adhesive, such as a glue, can provide fixation of the projections to the bone anchors 22 inside the cavities 66.

It should thus be appreciated that the implant body 24 includes at least one engagement member 27, and the bone anchors 22 includes a complementary engagement member 29 configured to mate with the engagement member 27 of the implant body 24 so as to secure the bone anchors 22 to the implant body 24. In one embodiment, the engagement member 27 of the implant body 24 can be provided as a recess, such as the recess 32. In another embodiment, the engagement member 27 of the implant body 24 can be provided as a protrusion, such as the protrusion 64. In one embodiment, the engagement member 29 of the bone anchors 22 can be a protrusion in the form of the head 42 that is received in the recess 32. In another embodiment, the engagement member 29 of the bone anchors 22 can be a cavity such as the cavity 66 formed in the head 42 that is configured to receive the protrusion 64. The implant body 24 and the bone anchors 22 can include any alternatively constructed engagement member suitable to fix the bone anchors 22 to the implant body 24 such that the bone anchors 22 can also be fixed to the vertebral bodies 38 and 40.

With continued reference to FIGS. 12 and 13, in one embodiment, the intervertebral implant 20 comprises an implant body 24 defining the central axis 26, the first bone contacting surface 28 that is arranged transversely to the central axis 26, and the second bone contacting surface 30 that is arranged transversely to the central axis 26. The implant body 24 further includes a number of projections 64 that extend from the first bone contacting surface 28 along the transverse direction T and/or a number of projections that extend from the second bone contacting surface 30 along the transverse direction T. The implant 20 can further include a number of bone anchors 22 each having the shaft 36 that is configured to be anchored to bone and the head 42 that defines the cavity 66 configured to engage one of the projections 64. The implant body 24 can further comprise a number of projections 66 that extend from the first bone contacting surface 28 in the transverse direction T and a number of projections 66 that extend from the second bone contacting surface 30 in the transverse direction T. The bone anchors 22 can be only held form-fittingly on the projections 66. This configuration prevents lateral movement of the heads 42 relative to the implant body 24. Each projection 64 can fit loosely in a cavity 66 in an axial direction so that, after completing the insertion of the intervertebral implant, the bone anchors 22 can be glued or otherwise fixed in place to the implant body 24 by the surgeon. Thus, the bone anchor 22 can initially engage the projections 64 with a loose fit. Then, a polymerizeable mass can be introduced into the cavities 66 so that the heads 42 of the bone anchors 22 polymerize with the mass. The heads 42 of the bone anchors 22 are connectable to the projections 64 via a harndenable substance, such as glue, cement or a polymerizable monomer or comonomer.

With continued reference to FIGS. 12 and 13, in another embodiment, the bone anchors 22 can be fixable in a stable manner through the projections 64. The number of projections 64 can be between one and four, so that each bone anchor 22 engages one projection 64. The number of projections 64 that extend from the first bone contacting surface 28 can differ from the number of projections 64 that extend from the second bone contacting surface 30, and vice-versa. The heads 42 of the bone anchors 22 can be mechanically connectable to the projections 64, via, for instance, a plug-in connection. In a plug-in connection, the projections 64 are inserted inside the cavities 66. This plug-in connection can be a uni-directional plug-in connection. In a uni-directional plug-in connection, a projection 64 is inserted inside a cavity 66 so that the bone anchor 22 can only move in one direction. For instance, in an uni-directional plug-in connection, when the projection 64 is inserted inside the cavity 66, the bone anchor 22 can only move in the transverse direction T. In use, upon connection of the heads 42 to the projections 64, there is no axial or lateral clearance between each of the heads 42 of the bone anchors 22 and the projections 64. The heads 42 of the bone anchors 22 can be removably connected to the projections 64 via a uni-directional plug-in connection as described above. The bone anchors 22 can be in the form of pins or screws. The bone anchors 22 can be cannulated and can comprise radial perforations as described above with respect to the embodiment illustrated in FIG. 7. For instance, the bone anchors 22 can define a cannulation or bore 54 (FIG. 7) extending along the transverse direction T along the shaft 36 and the head 42. Radial perforations 56 (FIG. 7) are in fluid communication with the cannulation 54 (FIG. 7) and extend from the cannulation 54 through the wall forming the shaft 36 along the longitudinal direction L and along the lateral direction A. Bone cement can be injected through the cannulation 54 (FIG. 7) and the radial perforations 56 (FIG. 7) into the bone. The bone anchors 22 can be configured as staples each comprising two or more substantially parallel pins configured to be anchored to bone as described above with respect to FIGS. 9-11. The heads 42 of the bone anchors 22 can be removably connected to the projections 64 in an oblique direction relative to the central axis 26 of the implant body 24.

Figure 14:
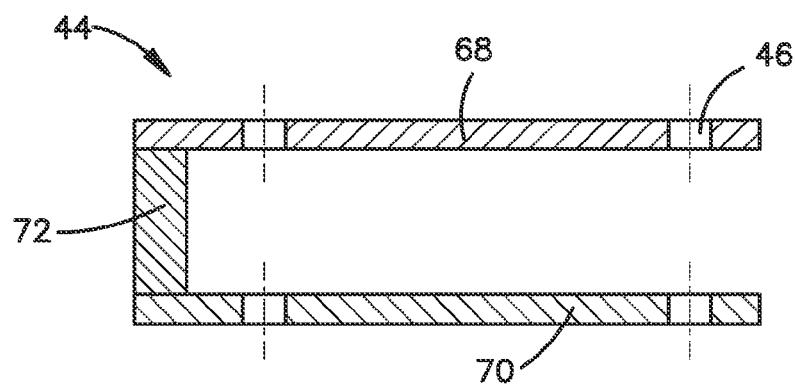
FIG. 14 is a sectional elevation view of a template constructed in accordance with one embodiment.
Figure 15:
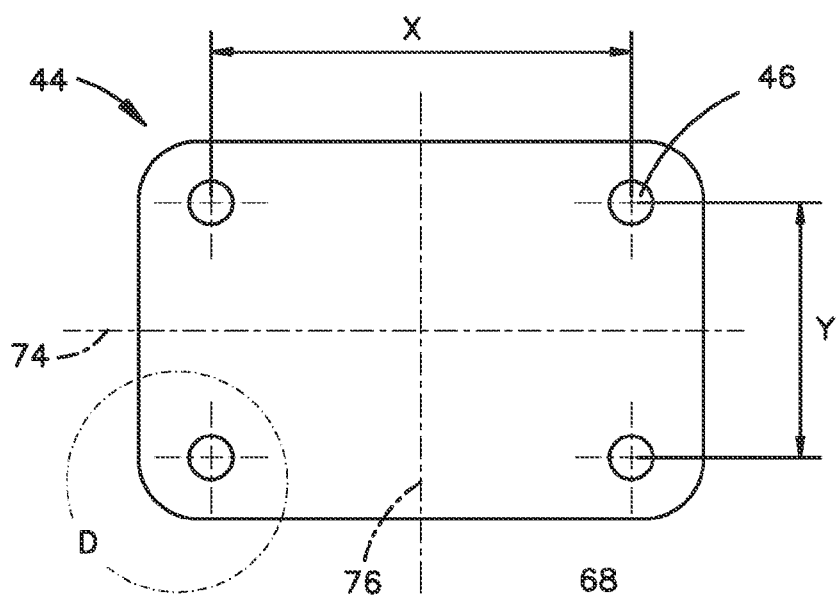
FIG. 15 is a top plan view of the template illustrated in FIG. 14.

Referring now to FIGS. 14 and 15, an intervertebral implant assembly can include the implant 20 and a template 44 that is configured to properly position the bone anchors 22 such that they are aligned with the engagement members (e.g., recesses 32 or projections 64) prior to inserting the bone anchors 22 into the vertebral bodies 38 and 40. The template 44 includes a first or upper plate 68, a second or lower plate 70 that is transversely spaced from the upper plate 68, and a spacer 72 disposed between the upper and lower plates 68 and 70, for instance at an end of the plates 68 and 70.

The upper and lower plates 68 and 70 can be elongate along a central longitudinally axis 74 and a central lateral axis 76. The template 44 includes number one or more aiming holes 46 that extend transversely through the upper and lower plates 68 and 70. In the illustrated embodiment, the aiming holes 46 are spaced along the longitudinal distance X, and the lateral distance Y, such that the aiming holes 46 are arranged so as to correspond to the arrangement of the engagement members of the implant body 24. The aiming holes 46 can be substantially cylindrical as illustrated in FIG. 15 and can be sized substantially equal to or greater than the heads 42 of the bone anchors 22. Accordingly, during operation, after the bone anchors 22 have been inserted through the aiming holes 46 and into the respective vertebral bodies 38 and 40, the template 44 can be displaced along the transverse direction so as to allow the spherical heads 42 of the bone anchors 22 to pass through the passage holes 46.

Figure 16:
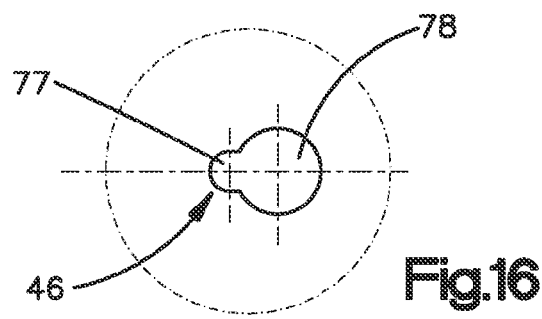
FIG. 16 is an enlarged top plan view of a portion of a template similar to Region D illustrated in FIG. 15, but constructed in accordance with an alternative embodiment.

Alternatively, referring to FIG. 16, the aiming holes 46 can be key-hole shaped having a first aiming portion 77 and a passage 78 connected to the aiming portion 77 and horizontally (e.g., longitudinally) offset from the aiming portion and defining a size that is greater than the aiming portion 77. The aiming portion 77 can have a shape that is sized substantially the same as at least a portion of the bone anchor shaft 36, so as to ensure that the bone anchor 22 is accurately positioned in the vertebral bodies 38 and 40 when the shaft 36 is inserted through the aiming portion 77. The passage 78 can be sized greater than the shaft 36 and the head 42, such that once the bone anchors have been inserted into the vertebral bodies through the aiming portion 77, the template 44 can be translated longitudinally so as to align the passages 78 with the bone anchors 22. The template 44 can then be translated in the transverse direction to slide the passages 78 over the heads 42 and remove the template 44 from the intervertebral space 37. A number of aiming holes 46 can be provided in the template 44 in an arrangement that corresponds to the arrangement of the recesses 32 or projections 64 of the implant 20. Any of the methods for fixing an implant described herein can further comprise the step of setting one or more bone anchors using the template 44 which includes one or more aiming holes 46 that position the one or more bone anchors 22 as desired in one or each of the first and second vertebral bodies 38, 40 so that the bone anchors 22 are engageable with recesses 32 or projections 64.

Referring now to FIGS. 17-20, the intervertebral implant 20 includes the implant body 24 and at least one bone anchor 22. In accordance with the illustrated embodiment, the recess 32 can be sized to receive a number of anchor heads 42. Thus, the engagement member 27 of the implant 20 can be configured to receive at least one, such as a number of bone anchors 22, so as to fix the received bone anchors 22 to the implant body 24. The bone anchors 22, such as screws, pins or other bone anchors can be coupled two by two. The first and second bone contacting surfaces 28 include one recess 32 in accordance with the illustrated embodiment. Thus, the implant 20 can include at least one recess 32 in both surfaces 28 and 30, such that the recess 32 retains at least one up to all of the bone anchors 22 that are fixed to the implant body 24 at the respective surfaces 28 and 30. Thus, a number of bone anchors 22 set in the natural endplate 39 or 41 of the same vertebral body 38 or 40 can engage one recess 32 on the respective bone contacting surface 28, 30 of the implant body 24. The number of recesses 32 in the first bone contacting surface 28 can differ from the number of recesses 32 in the second bone contacting surface 30, and vice-versa.

The recesses 32 are illustrated as substantially rectangular having a longitudinal length L and a lateral width W. The length L and the width W of each recess 32 are dimensioned such that the head 42 of the number of (e.g., four) bone anchors 22 can be positioned in the recess. The shafts 36 of the bone anchors 22 can be threadedly driven or otherwise inserted into the first and second vertebral bodies 38 and 40. The heads 42 can be configured as screw heads which are placed in the respective recess 32 and fixed to the implant body 24 via a hardenable substance 48 that is injected into the recess 32, or any alternative mechanical fastener. As illustrated in FIG. 17, the bone anchors 22 can be oriented such that their central axes extend substantially parallel to the central axis 26 of the implant body 24. The bone anchors 22 can be implanted in the vertebral bodies 38, 40 at an angle of 90° with regard to the surface of the endplate 28. 30. Alternatively, the bone anchors 22 can be oriented such that their central axes are oblique with respect to the central axis 26. For instance, the central axes of the bone anchors 22 can diverge from each other in a transverse direction out from the implant body 24 toward the tips 80, or can alternatively converge toward each other in a transverse direction out from the implant body 24 toward the tips 80. The bone anchors 22 can be implanted in the vertebral bodies 38, 40 at an angle deviating from 90° with regard to the surface of the endplate 28, 30. The bone anchors 22 can include bone screws, pins or staples. The heads 42 of the bone anchors 22 can engage with the recesses 32 so that the bone anchors 22 are in an oblique direction oblique relative to the central axis 26 of the implant body 24.

It should be appreciated that any of the engagement members or surfacing defining the recesses of the previously described embodiments (.e.g., surfaces 35, 51, or 57) or the surfaces defining the cavity 66 can include a shape changing component or be made at least partially from a shape memory material, such as a shape memory polymer or a shape memory alloy. The shape memory material will be configured to have a first, initial, configuration and a second, fixing, configuration. In the initial configuration, the shape memory material allows the bone anchor to be positioned in the recess. In the fixing configuration, the shape memory material moves to hold fixedly the bone anchor in the recess. The transition from the initial to the fixing configuration is activated by the application of light or heat thereto, though it is appreciated that other activation methods are available depending on the shape memory material. The process of transitioning the shape memory material from the initial configuration to the fixing configuration can of course be reversed from the fixing configuration to the initial configuration as desired.

The shape memory material can be any suitable material as desired. For example, the shape memory material could include polymers such as thermoplastic multiblock copolymers like polyurethanes, polyesterurethanes or multiphase polymer networks like poly(ϵ-caprolactone)dimethacrylate and n-butyl acrylate, multiblock copolymers containing poly (L-lactide) and poly[glycolide-co-(ϵ-caprolactone)]-segments. The shape memory material could also be an alloy such as NiTi, Ag—Cd 44/49 at. % Cd, Au—Cd 46.5/50 at. % Cd, Cu—Al—Ni 14/14.5 wt. % Al and 3/4.5 wt. % Ni, Cu—Sn approx. 15 at. % Sn, Cu—Zn 38.5/41.5 wt. % Zn, Cu—Zn—X (X=Si, Al, Sn), Fe—Pt approx. 25 at. % Pt, Mn—Cu 5/35 at. % Cu, Fe—Mn—Si, Pt alloys, Co—Ni—Al, Co—Ni—Ga, Ni—Fe—Ga, Ti—Pd in various concentrations, Ni—Ti (~55% Ni), Ni—Ti—Nb, and Ni—Mn—Ga.

The bone anchors can include a mechanical interlocking mechanism, such as threads, a ratchet mechanism or shaft, that expands in volume by an introduction of gas, water or vapor creation or via a shape changing component, such as shaft 36, component comprising a shape memory material (e.g. a shape memory polymer or a shape memory alloy) to fix the bone anchors to the vertebral bodies. Suitable shape memory polymers may include thermoplastic multiblock copolymers like polyurethanes, polyesterurethanes or multiphase polymer networks like poly(ϵ-caprolactone) dimethacrylate and n-butyl acrylate, multiblock copolymers containing poly(L-lactide) and poly[glycolide-co-(ϵ-caprolactone)]-segments. Suitable shape memory alloys may include NiTi, Ag—Cd, Cu—Al—Ni, Cu—Sn, Cu—Zn, Cu—Zn—X (X=Si, Al, Sn), Fe—Pt, Mn—Cu, Fe—Mn—Si, Pt alloys, Co—Ni—Al, Co—Ni—Ga, Ni—Fe—Ga, Ti—Pd, Ni—Ti—Nb, and Ni—Mn—Ga A bone screw combination can be used to fix the implant to the vertebral bodies, such as a first screw that extends through the head of a second screw.

With reference to FIG. 21, it should be further appreciated that a suture 82 can be used to fix the bone anchor 22 in the recess 32 of the implant body. The bone anchor 22 and recess 32 may be any or a combination of the bone anchors 22 and recesses 32 described of the type described herein. The suture 82 can provide the primary fixation and/or can be used in conjunction with any of the other engagement members previously described to fix the bone anchor 22 to the implant body 24. The suture 82 may be a single thread or a double thread.

In this further embodiment, the implant body 24 can define a channel 84 that starts from a location in the recess 32 and ends at an opening 86 on a surface of the implant body 24, which can be a non-bone contacting surface. Thus, the channel 84 comprises at least one first opening 92 located at or near the recess 32, or any other engagement member 27, the second opening 86 on a surface of the implant body 24 other than a bone-contacting surface 28, 30, and one or more passageways 94 extending between the first opening 92 and the second opening 86. The opening 86 is accessible to, for example, a surgeon when a bone contacting surface abuts or is engagement with bone. The channel 84 allows the suture 82 to be passed from the bone anchor 22 to the surface where it is tied in order to fix the bone anchor 24 to the implant body 24. The head 42 of the bone anchor 22 can define an eyelet or hole 88 configured and sized to receive at least a portion of the suture 82. The suture 82 can be inserted through the hole 88 and positioned around the head 42, and then tied to the head 42. The channel 84 may be a single passageway or may be two closely aligned passageways.

In the variant of the channel 84 where the single passageway is used, the suture 82 is tied in a suitable configuration to provide an anchoring object to prevent the suture from withdrawing into the channel 84. The anchoring object could be a suitable knot 90, as illustrated, or the suture could be fixed to a body that serves as the anchoring object.

In the embodiment where the implant body features two closely aligned passageways, the two passageways are separated by a part of the surface of the implant body. The surgeon will thread a strand of the suture, for example the double threaded suture, down either passageway and can then tie those strands together to thereby use the part of the surface as an anchoring object.

In one embodiment, the bone anchors 22 can be fixed by preliminary insertion of a suture 82 into the implant body 24. The endplate may comprise a channel in which a suture 82 is fixedly retained. The channel 84 may comprise at least one passageway 94. The channel 84 may have an opening 92, 86 in both a recess and on a non-bone contacting surface. The suture 82 may be fixed to the implant body 24 using an anchoring object such as a knot 90 in the suture 82, an external body and/or a part of the implant body 24. In one embodiment, a kit can comprise the implant 20 and the template 44.

An intervertebral implant kit can include at least one implant body 24 such as a number of implant bodies 24, at least one bone anchor 22 such as a number of bone anchors 22, and/or at least one template 44 such as a number of templates 44. The implant bodies 24 can be constructed in accordance with any of the embodiments described herein, and can be constructed the same as or differently from each other. The bone anchors 22 can be constructed in accordance with any of the embodiments described herein, and can be constructed the same as or differently from each other. The templates 44 can be constructed in accordance with any of the embodiments described herein, and can be constructed the same as or differently from each other.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present disclosure.

The invention claimed is:

1. An intervertebral implant assembly comprising:
   an intervertebral implant body defining a first bone contacting surface and a second bone contacting surface spaced apart from the first bone contacting surface along a central axis, at least one of the first and second bone contacting surfaces defining at least one recess that extends into the implant body but not through the implant body, and at least one recess opening for each respective recess, the at least one recess opening extending transversely with respect to the central axis and being aligned with the respective first and second bone contacting surfaces, the at least one recess opening being sized to receive a head of a bone anchor therethrough so that a shaft of the bone anchor extends out from the respective at least one of the first and second bone contacting surfaces when the at least one recess receives the head of the bone anchor, wherein the at least one recess opening is configured to receive the head of the bone anchor after the shaft has been inserted into a vertebral body.

2. The implant assembly according to claim 1, further comprising the at least one bone anchor, the at least one bone anchor comprising a shaft extending from the head, the shaft configured to be inserted in a vertebral body.

3. The implant assembly as recited in claim 2, wherein the at least one recess extends into the implant body in a transverse direction.

4. The implant assembly according to claim 3, wherein the recess is configured as a pocket hole penetrating into the implant body from the first and second bone contact surfaces.

5. The implant assembly according to claim 3, wherein the head is press-fit into the at least one recess.

6. The implant assembly according to claim 3, wherein the head is loosely received in the at least one recess.

7. The implant assembly according to claim 3, wherein the head is secured to the implant body by a hardenable substance that is injected into the at least one recess.

8. The implant assembly according to claim 7, wherein the hardenable substance includes a glue, a cement or a polymerizable monomer or copolymer.

9. The implant assembly according to claim 2, further comprising a suture for fixing the at least one bone anchor to the at least one recess.

10. The implant assembly according to claim 2, wherein surfaces defining the at least one recess are at least partially made of a shape memory material, the surfaces having an initial configuration, wherein the head fits loosely in the at least one recess, and a fixing configuration, wherein the head is tightly received within the at least one recess.

11. The implant assembly according to claim 1, further comprising a template that defines at least one aiming hole corresponding to the arrangement of the at least one recess of the implant body.

12. The implant assembly according to claim 11, wherein the at least one recess is a plurality of recesses, and the template comprises a plurality of aiming holes configured to be aligned with respective to one of the recesses of the implant body.

13. The implant assembly according to claim 12, wherein the aiming holes comprise a first aiming portion and a passage connected to the aiming portion and sized greater than the aiming portion.

14. The implant assembly according to claim 2, wherein the at least one bone anchor defines a bore that extends along the shaft and the head.

15. The implant assembly according to claim 14, wherein the shaft defines radial perforations in fluid communication with the bore.

16. The implant assembly according to claim 1, wherein the at least one recess is a first upper recess and a second upper recess, the first and second upper recesses extending from the respective first and second bone contacting surfaces.

17. The implant assembly according to claim 1, wherein the at least one bone anchor is oriented at an oblique angle with respect to the central axis.

18. The implant assembly according to claim 1, wherein the implant assembly is an intervertebral implant assembly.

19. The implant assembly according to claim 1, further comprising the at least one bone anchor, the at least one bone anchor configured as a staple.

20. The implant assembly according to claim 19, wherein the staple comprises a first pin, a second pin, and a bridge, the bridge interconnecting the first and second pins.

21. The implant assembly according to claim 20, wherein the bridge is press-fit inside the recess.

22. The implant assembly according to claim 20, wherein the bridge is loosely received within the recess.

23. The implant assembly according to claim 22, wherein the bridge is secured to the implant body by a hardenable substance that is injected into the recess.

24. The implant assembly according to claim 2, wherein the recess is sized to receive a plurality of heads.

25. The implant assembly according to claim 24, wherein all of the plurality of heads are secured to the implant body by a hardenable substance injected in the recess.

26. An intervertebral implant assembly comprising:
an intervertebral implant body sized to be received in an intervertebral space defined by a first vertebral body and a second vertebral body, the intervertebral implant body defining a first bone contacting surface configured to face the first vertebral body, and a second bone contacting surface configured to face the second vertebral body, the first bone contacting surface spaced apart from the second bone contacting surface, the implant body defining a first recess that extends into the first bone contacting surface but not through the implant body, the implant body defining a second recess that extends into the second bone contacting surface but not through the implant body, the implant body defining first and second openings into the first and second recesses, respectively;
a first bone anchor comprising a first head and a first shaft that extends from the first head along a first axis, the first recess sized to receive the first head; and
a second bone anchor comprising a second head and a second shaft that extends from the second head along a second axis, the second recess sized to receive the second head,
wherein the intervertebral implant body is configured to be inserted between the first and second vertebral bodies such that (i) the first opening aligns with and receives the first head along the first axis after the first shaft has been inserted into the first vertebral body and (ii) the second opening aligns with and receives the second head along the second axis after the second shaft has been inserted into the second vertebral body.

27. The implant assembly according to claim 26, wherein at least one of the first bone anchor or the second bone anchor is configured as a hook member.

28. The implant assembly according to claim 1, wherein the at least one recess includes a first plurality of recesses that extend from the first bone contacting surface into the implant body but not through the implant body, and a second plurality of recesses that extend from the second bone contacting surface into the implant body but not through the implant body.

29. The intervertebral implant assembly of claim 1, wherein the first bone contacting surface is spaced from the second bone contacting surface along a central axis, the implant body further defines a longitudinal axis that is substantially perpendicular to the central axis, and a lateral axis that is substantially perpendicular to the central axis and the longitudinal axis, wherein each of the lateral and longitudinal axes intersect the central axis at a common point of intersection, and the at least one recess is spaced from the common point of intersection.

30. The implant assembly according to claim 1, where the first and second bone contacting surfaces further defining a recess opening cross-sectional dimension that extends transversely with respect to the central axis and being aligned with the respective at least one of the first and second bone contacting surfaces, the recess opening cross-sectional dimension being sized so that the recess opening receives the head of the bone anchor therethrough.

31. The intervertebral implant assembly of claim 30, further comprising the at least one bone anchor, wherein the shaft of the at least one bone anchor extends from the head along a bone anchor axis, and the head of the at least one bone anchor defines a head cross-sectional dimension that extends along a transverse direction that is substantially perpendicular to the bone anchor axis, wherein the recess opening cross-sectional dimension is greater than or equal to the head cross-sectional dimension.

32. The implant assembly according to claim 1, wherein the at least one recess extends from the respective recess opening to a recess inner end that is spaced from the respective bone contacting surface, wherein the recess opening defines a recess opening cross-sectional dimension that is no less than a cross-sectional dimension of the recess aligned with the inner end of the recess alone the central axis.

33. The implant assembly according to claim 1, wherein the at least one recess is a first recess and a second recess aligned with the first recess along a line that is perpendicular to the central axis, the line lying on the respective first and second bone contacting surfaces, wherein when head is received by one of first recess and second recess, no portion of the line extends through the head.

* * * * *